US010259918B2

(12) United States Patent
Campos Beceiro

(10) Patent No.: US 10,259,918 B2
(45) Date of Patent: Apr. 16, 2019

(54) METHOD FOR PRODUCING A NON-BREATHABLE, MICRO-POROUS THERMOPLASTIC POLYMER FILM FOR OUTER COVERING OF DIAPERS AND SANITARY TOWELS

(71) Applicant: KLONER, S.L., Sant Andreu de Llavaneras (ES)

(72) Inventor: Alberto Campos Beceiro, Sant Andreu de Llavaneres (ES)

(73) Assignee: KLONER S.L., Sant Andreu de Llavaneres (ES)

( * ) Notice: Subject to any disclaimer, the term of this patent is extended or adjusted under 35 U.S.C. 154(b) by 198 days.

(21) Appl. No.: 15/267,519

(22) Filed: Sep. 16, 2016

(65) Prior Publication Data
US 2017/0002157 A1 Jan. 5, 2017

Related U.S. Application Data

(62) Division of application No. 14/364,332, filed as application No. PCT/ES2013/070003 on Jan. 10, 2013, now Pat. No. 9,447,247.

(30) Foreign Application Priority Data

Jan. 14, 2012 (ES) ................... 201230055

(51) Int. Cl.
B05D 1/26 (2006.01)
B29B 7/48 (2006.01)
B29B 7/90 (2006.01)
B32B 7/12 (2006.01)
C08J 5/18 (2006.01)
C08K 3/26 (2006.01)
C08K 9/04 (2006.01)
(Continued)

(52) U.S. Cl.
CPC ................ *C08J 5/18* (2013.01); *A61L 15/18* (2013.01); *A61L 15/20* (2013.01); *A61L 15/225* (2013.01); *A61L 15/24* (2013.01); *A61L 15/425* (2013.01); *A61L 15/58* (2013.01); *B05D 1/265* (2013.01); *B29B 7/48* (2013.01); *B29B 7/90* (2013.01); *B29C 47/0007* (2013.01); *B29C 47/0021* (2013.01); *B29C 47/0057* (2013.01); *B29C 55/02* (2013.01); *B32B 7/12* (2013.01); *B32B 27/08* (2013.01); *B32B 27/20* (2013.01); *B32B 27/205* (2013.01); *B32B 27/32* (2013.01); *C08K 3/26* (2013.01); *C08K 9/04* (2013.01); *C08L 23/0815* (2013.01); *C08L 23/0869* (2013.01); *C09J 151/06* (2013.01); *B29K 2023/0633* (2013.01); *B29K 2105/16* (2013.01); *B29L 2031/4878* (2013.01); *B32B 2264/104* (2013.01); *B32B 2555/00* (2013.01); *B32B 2555/02* (2013.01); *C08J 2323/06* (2013.01); *C08J 2451/06* (2013.01); *C08K 2003/265* (2013.01); *Y10T 428/249978* (2015.04)

(58) Field of Classification Search
CPC ......... B05D 1/265; C08J 5/18; C08J 2451/06; C08J 2323/06; C08L 23/0869; C08L 23/0815; C08K 9/04; C08K 3/26; C08K 2003/265; A61L 15/24; A61L 15/58; A61L 15/20; A61L 15/18; A61L 15/425; A61L 15/225; B29C 47/0021; B29C 47/0057; B29C 55/02; B29C 47/0007; B29B 7/90; B29B 7/48; C09J 151/06; B32B 27/205; B32B 7/12; B32B 27/08; B32B 27/32; B32B 27/20; B32B 2555/00; B32B 2264/104; B32B 2555/02; B29K 2105/16; B29K 2023/0633; B29L 2031/4878; Y10T 428/249978
USPC ................................ 264/176.1, 211, 211.12
See application file for complete search history.

(56) References Cited

U.S. PATENT DOCUMENTS 3,922,427 A  11/1975 Toyoda et al.
6,258,308 B1 * 7/2001 Brady ............... A61F 13/51462
                                              264/210.2
(Continued)

FOREIGN PATENT DOCUMENTS

WO   2001/85832  A2   11/2001
WO   2005/021262 A1   10/2005

OTHER PUBLICATIONS

Renner Ket al. "Quantitative determination 1-8 of interfacial adhesion in composites with strong bonding". European Polymer Journal, 2010, vol. 46, No. 10, pp. 2000-2004 .ISSN 0014-3057. 30 See Section 2, Experimental.

(Continued)

Primary Examiner — William P Fletcher, III

(57) ABSTRACT

A method for producing a non-breathable micro-porous thermoplastic polymer film for outer covering of diapers and sanitary towels includes a dispersion step by mixture of mineral particles surface-covered with a hydrophobic layer of fatty acid, a base polymer and a co-polymer adhesive, wherein the co-polymer adhesive is selected to comprise the base polymer; and film forming step in a film extrusion line having a flat film extruder provided with an extrusion nozzle, wherein the mixture is fed to the flat film extruder forming the film, and hot stretching the film between the extrusion nozzle and the solidification of the formed film, thereby obtaining the non-breathable micro-porous film with pores sizing from 0.5 to 5 μm without communication between the pores. The process requires less raw materials with a further reduction of film thickness, while giving a matt appearance to the film, thus making the usual micro-embossing step of the extrusion line unnecessary.

6 Claims, 1 Drawing Sheet

(51) Int. Cl.
*A61L 15/18* (2006.01)
*A61L 15/20* (2006.01)
*A61L 15/22* (2006.01)
*A61L 15/24* (2006.01)
*A61L 15/42* (2006.01)
*A61L 15/58* (2006.01)
*B29C 55/02* (2006.01)
*B29K 23/00* (2006.01)
*B29L 31/48* (2006.01)
*B32B 27/08* (2006.01)
*B32B 27/20* (2006.01)
*B32B 27/32* (2006.01)
*C08L 23/08* (2006.01)
*B29C 47/00* (2006.01)
*C09J 151/06* (2006.01)
*B29K 105/16* (2006.01)

(56) References Cited

U.S. PATENT DOCUMENTS 6,682,775 B2 * 1/2004 Calhoun .................. C08J 5/18
427/215
2004/0087235 A1 * 5/2004 Morman ............ A61F 13/4902
442/394

OTHER PUBLICATIONS

RT Vanderbilt Company, Inc. "Non-black fillers 1-8 for rubber" [on line] Jun. 1, 2009 [retrieved Apr. 2, 2013]. Retrieved from Internet: <http://www.rtvanderbilt.com/NonBlackFillers.pdf>.

Yan, H. et al "Hydrophobic magnesium hydroxide nanoparticle via oleic acid and poly(methyl methacrylate )-grafting surface modification". Powder technology, 2009, vol. J 93, pp. 125-129.

Zoukrami, F. et al. "Elongational and Shear Flow Behavior of Calcium Carbonate Filled low density Polyethylene: effect of Filler Particle Size, Content, and Surface Treatment". Journal of Applied Polymer Science, 2012, vol. 123, pp. 257-266.

* cited by examiner

METHOD FOR PRODUCING A NON-BREATHABLE, MICRO-POROUS THERMOPLASTIC POLYMER FILM FOR OUTER COVERING OF DIAPERS AND SANITARY TOWELS

CROSS-REFERENCE TO RELATED APPLICATIONS

This U.S. patent application is a divisional application of a granted U.S. patent Ser. No. 14/364,332 filed on Jan. 10, 2013, a national stage application of PCT/ES2013/070003 filed on Jun. 11, 2014, claiming priority under 35 U.S.C. 119 (a) through (d) from a Spanish patent application P201230055 filed on Jan. 14, 2012, hereby entirely incorporated by reference.

BACKGROUND OF THE INVENTION

Field of the Invention

The present subject matter relates to a process for obtaining a non-breathable, micro-porous thermoplastic polymer film for outer covering of diapers and sanitary towels.

Description of Related Art

On the market there are two different types of outer covering for disposable diapers and sanitary towels, the first type consists of a matt polyethylene film, 18-22 μm thick, the second is obtained by lamination or co-extrusion of a 10-22 μm thick polyethylene film with an unwoven polypropylene fabric to give it a more textile appearance.

Both types may be breathable or non-breathable.

Breathable films have a water vapour permeable micro-porous structure that is impermeable to liquid water by capillary pressure. U.S. Pat. No. 6,682,775 by Imerys describes that this structure is obtained by loading a polymer with an important percentage of mineral particles treated superficially with a waterproofing substance that is non adhesive to the base polymer, then extruding the compound mixture as a film by any of the known technologies and subjecting it to single or bi-directional stretching of 1.2-2.5 times in order to increase the size of the pores and join them together.

The non-breathable films are obtained by extrusion and micro embossing of low-density polyethylene, generally linear using titanium dioxide pigments to obtain the desired whiteness and opacity.

Depending on the type of machinery used to make the diapers, and more specifically of the tensions the film is subject to in its passage through this machinery, more or less thickness of the film is necessary to guarantee its dimensional stability. Thus, older machines use films of up to 22 μm and more modern machines use around 18 μm thickness.

SUMMARY OF THE INVENTION

The Applicant intends to obtain a micro-porous structure with pores of smaller size than in breathable films and not joined to each other, hence not breathable, so a significant reduction of density is achieved at the same time as thanks to the fact that they maintain good mechanical properties at low tensions, they can be manufactured in less thickness, maintaining enhanced dimensional stability in the machines making diapers.

DETAILED DESCRIPTION

Figure 1:
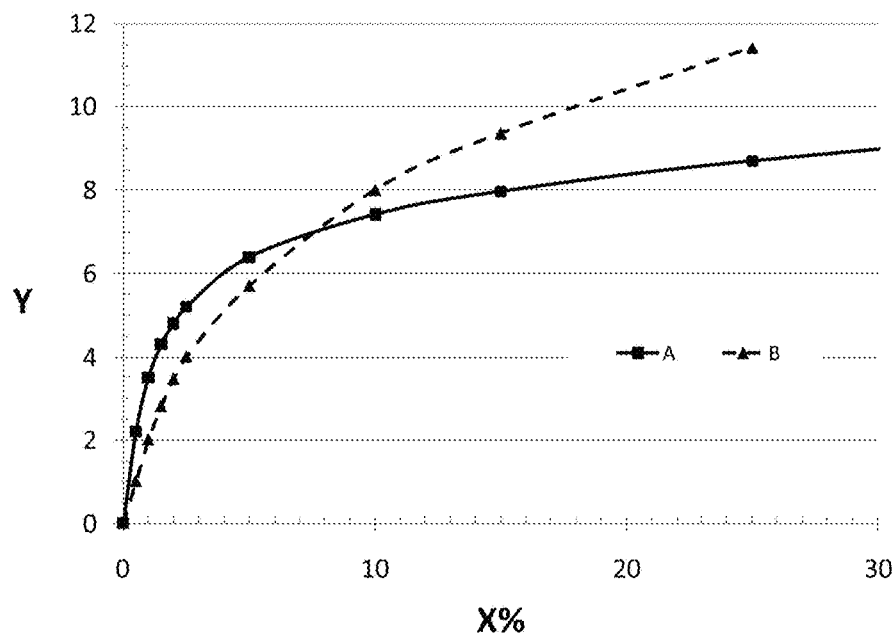
FIG. 1 illustrates a tension-elongation graph obtained according to embodiment no. 1 and from a 21 μm commercial film
X: Elongation in %
Y: Tension in MPa
A: Curve of the embodiment no. 1 film
B: Curve of a 21 μm commercial film
Figure 2:
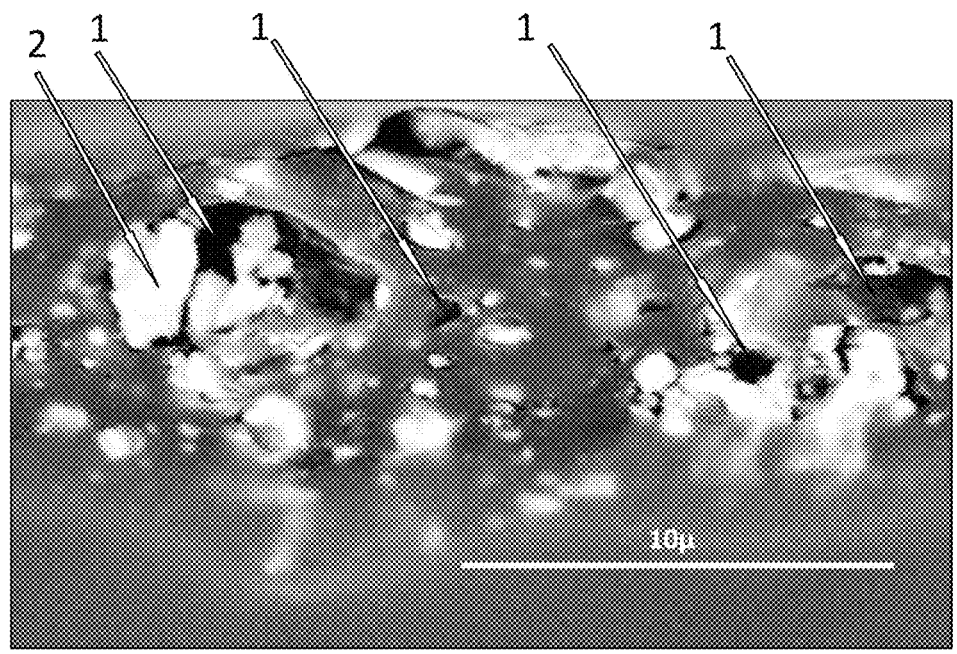
FIG. 2 illustrates a microphotograph of a cross section through the film corresponding to embodiment number 1.
1: micro-pores
2: particles of calcium carbonate

Preparation of the polymer compounded film with the mineral load.

Selection of the Polymer:

The selected polymer is a polyolefin, for instance and not limited to polyolefins of ethylene, of propylene, or butylene, such as polypropylene, high density polyethylene, medium and low density polyethylene and co-polymers. Low-density polyethylene is preferred and linear low-density polyethylene is more preferably, with a fluidity rate between 1 and 12 (g/10 min at 190° with 2.16 kg) and preferably between 4 and 8. The polymer will be dosed in a mass proportion of 30%-70%, preferably between 40 and 60%.

Selection of the Mineral Load:

The mineral load may be any inorganic compound habitually used in the plastics industry such as for instance (and not limited to) Talc, Kaolin, Calcium or Barium Sulphate, micro-spheres of glass and, preferably Calcium Carbonate.

The size of the particles will subsequently configure the size of the pores and their relative insulation, thus, excessively large particles will tend to produce large-sized pores in open structures, the average size of the particles should be between 0.5 and 4 μm and preferably between 1 and 2 μm to achieve a pore size of 0.2-5 μm.

With the aim of improving dispersion and reducing the adhesion of the particles of the mineral load with the polymer and thus facilitate the formation of the porosity, the particles should have their surface covered with a hydrophobic layer which in addition is incompatible with the polymer used. Any fatty acid commonly used to cover mineral loads such as for instance (and not limited to) stearic, palmitic, oleic, montanic, lauric acids may be used, in a mass proportion of 0.1%-0.5% with regard to the mineral load.

The mineral load will be dosed in a mass proportion of 30%-70%, preferably between 40% and 60%.

Selection of the Adhesive:

The lack of adhesion between the polymer and the particles of the mineral load gives rise to excessively poor mechanical features of the film obtained and, for the same reason, makes control of the size of the micro-pores more difficult, significantly increasing the presence of large-sized pores.

Thus it is necessary to improve the adhesion between the particles of the mineral load and the polymer, for which purpose an adhesive selected from the group comprising co-polymers of the base polymer used with graft polar groups such as for instance (and not limited to) maleic anhydride or acrylic acid. Silane or titanates can also be used.

The adhesive will be dosed in a mass proportion of 1%-5%, preferably between 1.5% and 3%.

In a preferred embodiment, the adhesive consists of a co-polymer of polyethylene with maleic anhydride for a base polymer consisting in a linear low-density polyethylene.

Procedure:

The procedure to obtain the compounded film has two steps; a step of dispersion of the particles of mineral load with the polymer and a film forming step.

The step where the mineral loads are dispersed in the polymer may be carried out in a separate operation from known procedures for mixing polymers with loads such as Henschel type powder mixers; Arm mixers of the Brabender type or extruders—double or single worm gear mixers, but it will preferably be carried out directly in the film extrusion line, through a single or double screw extruder-mixer and more preferably a double screw extruder with a section for removal of gases by means of a vacuum pump with the aim of completely eliminating any moisture introduced by the mineral load that would cause defects on the surface of the film.

This extruder may be connected to the extruders of the film extrusion line by means heated piping so that the molten compound mixture will flow via these pipes to the film extrusion line extruders or directly replace the extrusion line extruders.

The step where the film is formed will be carried out by technology known as blowing or extrusion of the flat film, taking care so as not to stretch the film cold with the aim of obtaining a pore size from 0.5-5 µm without communication between the pores.

Advantages:

These films provide significant cost savings in comparison to those commonly used for making the outer covering of diapers and sanitary towels, this difference of cost can be specified in the following aspects:

More dimensional stability to low stretching, allowing a reduction of the film thickness to 14 microns without reducing its stability in diaper manufacturing machines, with up to 20% saving in raw materials.

Less intrinsic transparency of the film due to the effect of the mineral load, which allows a saving of up to 50% in titanium dioxide.

Replacement of up to 60% of the polymer by the mineral load with just a 10% increase in density, enabling a saving of up to 30% in raw materials costs.

The presence of an important percentage of mineral load in the composition of the compounded film substantially increases its thermal conductivity, enabling an increase of up to 20% in production capacity of the extrusion line.

At the same time, this mineral load increases surface roughness, improving the efficacy of adhesives used for assembling diaper and sanitary towel parts, while at the same time giving a matt appearance to the film, making the micro-embossing step of the extrusion line unnecessary.

DESCRIPTION OF THE PREFERRED EMBODIMENT

Embodiment No. 1

Composition:
Dowlex 2035G linear low-density polyethylene: from Dow Chemical, 50%
Mikhart MU 17T calcium carbonate from Provençale: 47%
Amplify GR20 adhesive from Dow Chemical: 3%

Procedure:

The components are mixed in a Buss 6 gk/h extruder, obtaining a compound mixture in the shape of granules of 1.264 g/cm3 density and a fluidity rate of 2.12 g/10 min. with 2.16 kg at 190° C. This compound mixture is fed into a Collin 10 kg/h flat film extruder, producing a single 15-µm layer and stretching it 22% between the extrusion nozzle and the refrigerated cylinder.

A film is obtained with the features detailed in TABLE 1, which is compared with a commercial film commonly used as the outer covering of diapers. Embodiment no. 1 presents:

10% more density with 47% less polymer.

Resistance to deformation by small loads 1.7 times greater, giving it great dimensional stability.

A moderate loss of resistance to breakage (29%).

TABLE 1

|  | Embodiment Number 1 | Commercial film | Units |
| --- | --- | --- | --- |
| Thickness | 14.1 | 21 | microns |
| Density | 1.04 | 0.95 | g/cm3 |
| Porosity (density reduction) | 18 | 0 | % |
| Surface weight | 14.6 | 19.9 | g/m2 |
| Resistance with 1% elongation | 3.5 | 2 | MPa |
| Resistance with 5% elongation | 6.4 | 5.7 | MPa |
| Resistance with 10% elongation | 7.4 | 8.6 | MPa |
| Resistance to SM breakage | 22.91 | 32.39 | MPa |
| SM breakage elongation | 189.5 | 600 | % |

The invention claimed is:

1. A method for producing a non-breathable film having a non-breathable micro-porous thermoplastic polymer film for an outer covering of diapers and sanitary towels, the method comprising:

dispersing mineral particles in a base polymer, the mineral particles being surface-covered with a hydrophobic layer of a fatty acid, including mixture of the mineral particles, the base polymer, and a co-polymer adhesive selected from the group comprising co-polymers of the base polymer, wherein the base polymer is dosed in a mass proportion between 40-60%, the mineral particles are dosed in a mass proportion between 60-40% being surface-covered with the hydrophobic layer of fatty acid dosed in a mass proportion between 0.1-0.5% with regard to the mineral particles, and the co-polymer adhesive is dosed in a mass proportion between 1.5-3%; and forming a film in a film extrusion line having a flat film extruder provided with an extrusion nozzle, wherein the mixture is fed to the flat film extruder forming the film, and hot stretching the film between the extrusion nozzle and the solidification of the formed film, thereby obtaining the micro-porous film having pores not joined between each other.

2. The method according to claim 1, wherein the dispersion step is performed apart from the film extrusion line by mixers with arms, turbo-mixers for powder or single or multiple screw extruders-mixers.

3. The method according to claim 1, wherein the dispersion step is carried out directly in the film extrusion line, through a single or double screw extruder-mixer.

4. The method according to claim 1, wherein, in the film forming step, the film is subject to hot stretching sped between the extrusion nozzle and the solidification of the film at a relationship from 20/1 to 60/1.

5. The method according to claim 1, wherein the dispersion step is carried out apart from or directly in the film extrusion line through a double screw co-rotating extruders with gas removal assisted by a vacuum pump.

6. The method according to claim 1, wherein the thermoplastic polymer film obtained has a film thicknesses of 14 μm.

* * * * *